United States Patent [19]

Untermyer, II

[11] 4,243,886

[45] Jan. 6, 1981

[54] APPARATUS AND METHOD FOR THE MEASUREMENT OF NEUTRON MODERATING OR ABSORBING PROPERTIES OF OBJECTS

[75] Inventor: Samuel Untermyer, II, Portola Valley, Calif.

[73] Assignee: National Nuclear Corp., Redwood City, Calif.

[21] Appl. No.: 916,873

[22] Filed: Jun. 19, 1978

[51] Int. Cl.² .................................................. G01T 3/00
[52] U.S. Cl. ..................................... 250/390; 250/392
[58] Field of Search ................... 250/358 R, 359, 360, 250/363 S, 390, 391, 392

[56] References Cited

U.S. PATENT DOCUMENTS

| | | | |
|---|---|---|---|
| 3,532,883 | 10/1970 | Dresia et al. | 250/390 X |
| 3,544,793 | 12/1970 | Bless et al. | 250/390 X |
| 3,716,711 | 2/1973 | Olesen | 250/390 |

*Primary Examiner*—Davis L. Willis
*Attorney, Agent, or Firm*—Flehr, Hohbach, Test

[57] ABSTRACT

An apparatus and method for measuring the neutron moderating or absorbing properties of objects or materials in which a fast neutron source cooperates with a neutron absorbing material which reduces the energy of the fast neutrons by inelastic scattering so that they can be readily thermalized by a moderator. A thermal neutron detector is disposed adjacent the material and serves to detect thermal neutrons emitted by a moderator placed to receive and thermalize the reduced energy neutrons. A material whose absorption is to be measured is placed between a moderator and the detector.

11 Claims, 7 Drawing Figures

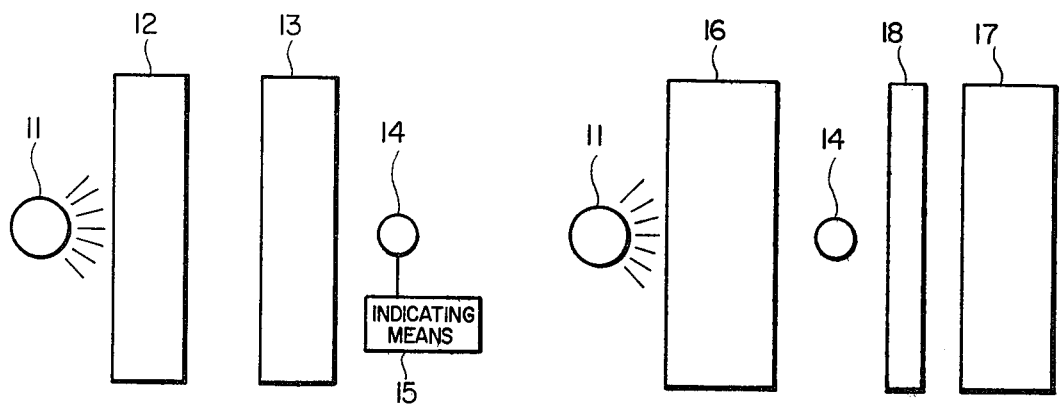
FIG_1 (PRIOR ART)   FIG_2
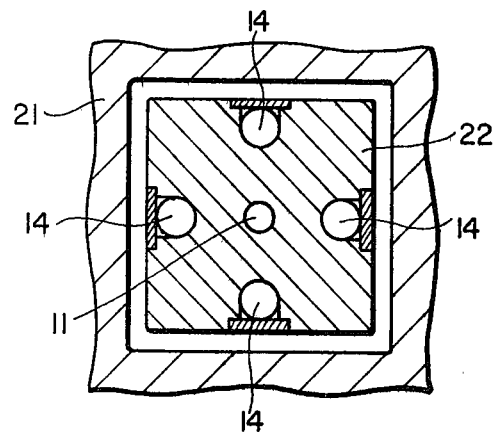
FIG_3
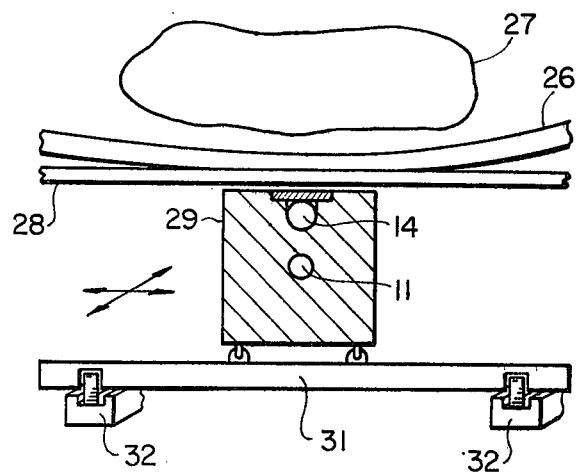
FIG_4

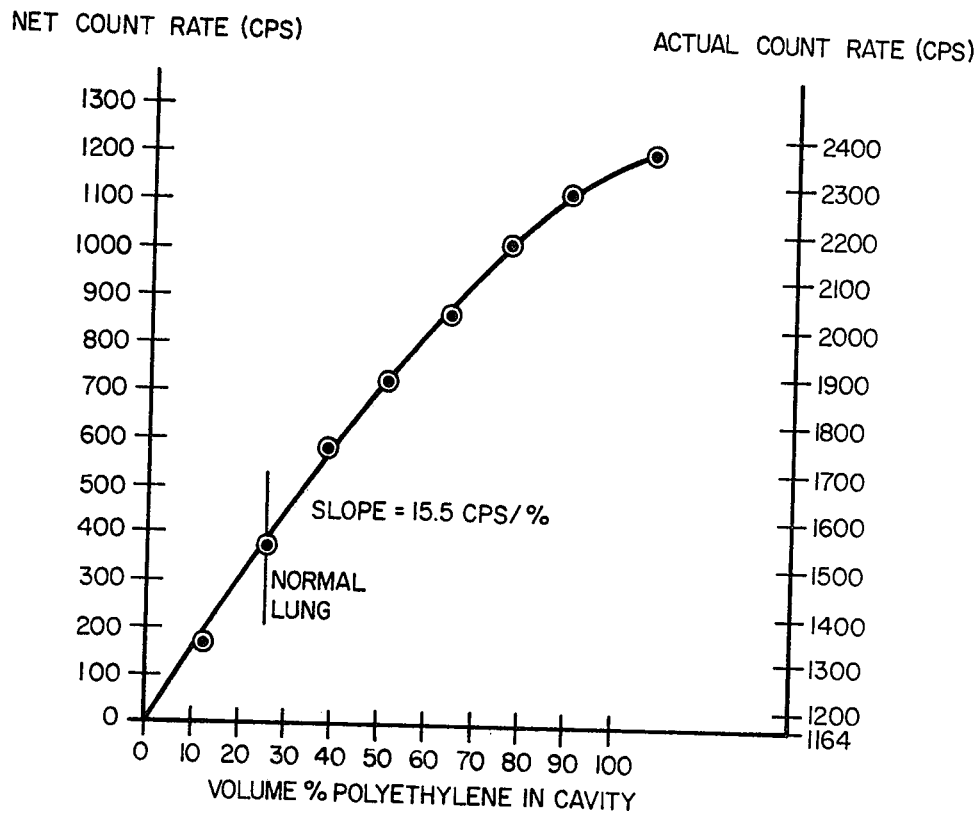
FIG_5
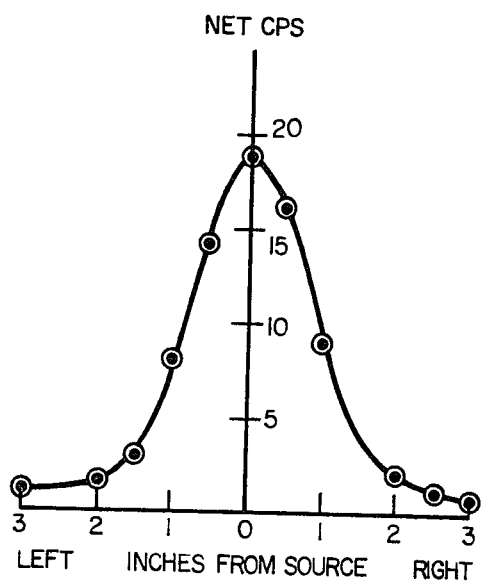
FIG_6
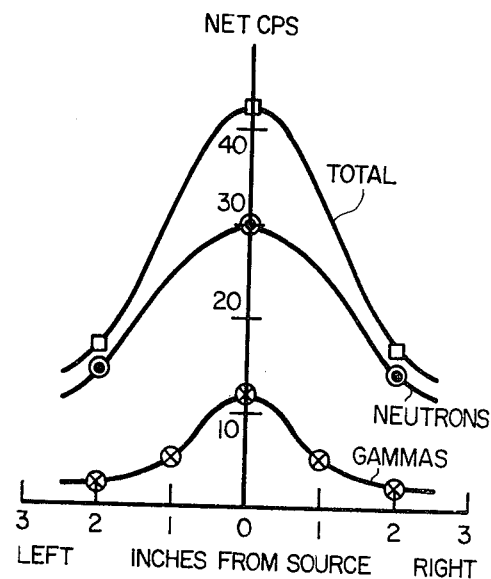
FIG_7

APPARATUS AND METHOD FOR THE MEASUREMENT OF NEUTRON MODERATING OR ABSORBING PROPERTIES OF OBJECTS

BACKGROUND OF THE INVENTION

This invention relates to the apparatus and method for the measurement of neutron moderating and absorbing properties of objects and more particularly to an apparatus which does not require transmission through the object being measured.

There is a need for the determination of the quantity of hydrogen in objects and also for the determination of the amount of neutron absorbers, such as boron, in nuclear fuel racks submerged under water. Presently such measurements are made by apparatus which relies on transmission through the object. Such an apparatus and method is schematically illustrated in FIG. 1. A source of fast neutrons 11 provides neutrons having energies in the range of 100–5,000 KEV. Such neutron sources are available from isotopic sources such as the spontaneous fission source, $Cf^{252}$, or alpha-neutron sources such as $Pu^{238}Be$. The high energy neutrons impinge upon the moderator 12 which thermalizes some of the neutrons into lower energy neutrons. The fast neutrons may, for example, be moderated by polyethylene material. Some of these thermal neutrons pass through the thermal neutron absorbing sample or object 13 and are detected by thermal neutron detector 14. The detector may be, for example, a $B^{10}F_3$ detector or a large $H^3$ detector. The detector 14 detects only thermalized neutrons and does not react or respond to fast neutrons. The output of the detector is applied to a counting or indicating means 15. A count is obtained in the absence of the object 13 so that the detector 14 counts the neutrons moderated in the moderator 12. The sample or object 13 is then interposed between the moderator 12 and detector 14 and a new count is obtained. The difference in counts is a measure of the absorbing or moderating properties of the object 13.

There are, however, many applications where it is not possible to place the sample between the moderator 12 and the detector 14. For example, there is need for a method and apparatus for the determination of hydrogen content of such materials as concrete and wood in the construction industry. It would be virtually impossible to place the detector on the other side of a concrete slab which is laid upon the ground.

Another example is the determination of the water content of the human lung. Such a determination would provide means for detecting the condition known as "pulmonary edema". However, most measurements presently performed for the detection of pulmonary edema are transmission measurements. It is relatively difficult to differentiate the water content of the lung from the other fluid content of the body both in front and in back of the lung. If a measurement could be made from the front of the body a large part of the interfering fluid content would be eliminated. There is also a need for the verification of the neutron absorbing properties of nuclear fuel storage racks during a period when the racks are immersed in water. Again, it is very desirable that this measurement be accomplished from one side, as for example, with a probe positioned in a location where the fuel is to be inserted.

As used herein, the term "moderator" refers to atomic species such as berylium, carbon and particularly hydrogen which reduced the energy of neutrons by elastic collisions. The term "inelastic scatter" refers to material such as iron, nickel or tungsten which principally reduced neutron energy by the discrete inelastic process of absorption and re-emission at lower energy. The terms "absorber" or "poison" refer to materials such as boron, cadmium or gadolinium which absorb thermal neutrons. In this connotation, thick sections of less absorbent material such as steel are considered poisons. The term "black" refers to an absorber which absorbs substantially all of the incident thermal neutrons. The term "neutron source" as used in this application refers either to an isotopic source of fast neutrons such as Pu-Be, PuLi, $Cf^{252}$, or to an accelerator neutron source such as a Van DeGraaf generator. The term "neutron detector" refers to a detector sensitive to thermal neutrons including such detectors as $BF_3$ or $He^3$ proportional counters and thermal neutron sensitive scintillation detectors. The term "fuel" or "nuclear fuel" as used herein refers to fresh or spent nuclear fuel elements containing sufficient fissionable material so that their storage requires special attention to criticality limits. The term "fuel storage racks" refers to special racks containing poison materials such as boron. The term "dry assay" refers to verification of the poison content of racks not flooded with water while the term "wet assay" refers to the assay after the racks are immersed in water. The individual openings in a fuel rack, accommodating one fuel element are described by the term "cell" and normally there are many cells in each fuel rack.

OBJECTS AND SUMMARY OF THE INVENTION

It is a general object of the present invention to provide a non-transmission method and apparatus for the measurement of neutron moderating and absorbing properties of objects and material.

It is another object of the present invention to provide a method and apparatus which will operate when access may only be obtained to one side of the moderating and/or absorbing object.

It is a further object of the present invention to permit the accurate measurement of poison concentration within cell walls of a fluid storage rack while the rack is immersed in water.

It is another object of the present invention to provide a method and apparatus for measurement of the hydrogen content of materials such as concrete in highway pavements and wood in large timbers where access to both sides of the sample is impractical.

It is still a further object of the invention to provide a method and apparatus for the measurement of hydrogen content of the human lung.

In general, the present invention comprises a source of fast neutrons, a thermal neutron detector disposed adjacent the material whose absorbing and/or moderating properties is to be measured, and non-moderating absorbing material disposed between the source and detector on the same side of the material as the detector. The invention is also directed to the method of measuring the neutron moderating or absorbing properties of a sample which comprises generating fast neutrons, passing said fast neutrons through non-moderating absorbing material, disposing said non-moderating absorbing material adjacent to the sample to be measured and placing a detector between said non-moderating absorbing material and said sample to detect thermal neutrons.

BRIEF DESCRIPTION OF THE DRAWINGS

FIG. 1 is a schematic diagram of apparatus in accordance with the prior art.

FIG. 2 is a schematic diagram of apparatus in accordance with the present invention.

FIG. 3 is a schematic diagram of apparatus for determining the presence of absorber in the walls of a fuel storage cell of a fuel storage rack.

FIG. 4 is a schematic diagram of apparatus for measuring the hydrogen or water content of the human lung.

FIG. 5 is a curve showing the effect of polyethylene test samples on count rate of apparatus of the type shown in FIG. 4.

FIG. 6 shows the spatial resolution of a system of the type shown in FIG. 4.

FIG. 7 is a curve showing the radiological exposure at the detector near the neutron source.

DESCRIPTION OF PREFERRED EMBODIMENTS

FIG. 1 which shows apparatus in accordance with the prior art has been described above.

Referring now to FIG. 2, apparatus in accordance with the present invention is illustrated. The apparatus includes a source of fast neutrons 11, of the type described with reference to FIG. 1, adjacent a mass of absorbing of poison material 16 which absorbs thermal neutrons. In this connection desirable materials include such materials such as thick sections of iron or nickel which scatter inelasticaly reducing the energy of fast neutrons to the range of 50–150 KEV. At this energy the neutrons can be more readily thermalized by a moderator such as a hydrogenous moderator 17. A thermal neutron detector, which will not detect neutrons having energies appreciably above a few electron volts, is disposed adjacent the non-moderating material 16 and on the same side of the moderator 17. The detector may be of the type previously described in connection with the description of FIG. 1.

A neutron absorber 18 is shown disposed between the thermal moderating material 17 and the detector 14. When the absorber 18 is present, the detector 14 will count very few neutrons since the fast neutrons which penetrate through the material 16 are not efficiently counted and all thermal neutrons generated by the material 17 are absorbed by the absorber 18. However, when the absorber 18 is removed, the fast neutrons, 50–150 KEV, passing through the non-moderating material 16 are moderated in the material 17 and generate thermal neutrons. The thermal neutrons are emitted from the surface, impinge upon the detector 14 and are counted. When the thermal neutron absorber 18 is replaced, the count rate decreases because the thermal neutrons produced are absorbed before they reach the detector 14. The extent by which the absorber reduces the count indicates the moderating or absorbing properties of the sample 17.

Thus, the moderating properties of the material 17 are measured by measuring with a detector on the same side as the neutron source thereby permitting nontransmission measurements, therefore the material 17 might comprise timber, concrete, the walls of a storage rack, the human lung or the like.

An experiment was carried out with apparatus of the type generally shown in FIG. 2. The components depicted in FIG. 2 were as follows:

| | |
|---|---|
| Neutron Source 11 | $2 \times 10^7$ Neutron/Second $Cf^{252}$ |
| Moderator, 17 | 6 inch by 6 inch by 12 inch polyethylene slab |
| Detector, 14 | 1 inch diameter, 10 inch active length, 70 cm $BF^3$ proportional counter |
| Non-moderating material 16 | 4 inch by 4 inch by 18 inch steel slab with source embedded |
| Absorber 18 | (a) 0.040 inch thick cadmium sheet |
| | (b) 0.013 g/cm$^2$ B10 |

The detector 14 was connected to a Baird Atomic Model 530 spectrometer. Power was supplied to the detector at 2,550 volts through a 1 megohm resistor. The following tests were made:

| | |
|---|---|
| Background, no source present | 3 counts per second |
| Source, no absorber 18 | 13,800 counts per second |
| Source, Cd absorber 18 | 1,233 counts per second |
| Source, B10 absorber 18 | 2,280 counts per second |
| Source, no absorber near detector but cadmium sheet perpendicular to slab | 13,400 counts per second |

As demonstrated by the above test, the absorber 18 had a large effect and it was possible to distinguish between stronger and weaker absorbers. Absorbers in other positions had little effect. The absorbing properties of an unknown material can be measured by comparing the counts obtained from the unknown material to those obtained from a merial whose absorption is known.

FIG. 3 shows a sectional view through a probe designed to fit into the cell of a fuel storage rack designated generally by the reference numeral 21. The source 11 is embedded in a steel block 22 approximately six inches in cross section. Four detectors 14 are positioned on four sides of the steel block 22. The absorber is, of course, the cell wall designated by 21 while the moderator is the water which surrounds the rack. By raising or lowering the probe along the vertical fuel storage cell the detectors provide a profile of the absorber distribution along each wall of the cell. Thus, there is provided a simple probe for measuring the absorption characteristics of a fuel cell storage rack.

FIG. 4 shows a schematic view of an apparatus for measurement of water in the human lung. More particularly, the front wall 26 of the chest cavity with the lung 27 adjacent thereto is schematically shown resting on a surface 28, such as the surface of a table which can be made of material such as aluminum or the like. The measuring apparatus or probe is beneath the table surface 28 adjacent the chest cavity. The probe consists of a block of steel which may, for example, be a 4-inch cube of steel 29 having imbedded therein a source 11. The source may, for example, be a $Pu^{238}$-Li which emits $10^6$ neutrons per second. The detector 14 may, for example, be a 10 atmosphere pressure, 1-inch diameter, 4-inch long $He^3$ proportional counter. As a preliminary to the use of the unit, the chest wall 26 can have its thickness measured by ultrasonic means in accordance with established technology. The detector face is then placed against the chest and counts are taken.

Using a plastic phantom to represent the human body a series of tests were made to test the viability of the measuring apparatus. For this purpose a phantom having a front chest wall represented by ¼ inch of plywood plus ⅜ inch of polyethylene was used. This thickness was selected since it was approximately equivalent to one inch of soft chest tissue. The back chest wall was represented by 3 inches of polyethylene, however the back wall had little effect on the results obtained by the method of the present invention. An 8-inch cavity was formed between these walls to represent the lung cavity. The cavity was loaded with various numbers of 1-inch thick polyethylene sheets to simulate various amounts of water in the lung. Measurements were made with various thickness of polyethylene in the lung cavity. Each measurement taken represented the average count rate over a 50 second counting period. The data which was obtained is shown in FIG. 5. The right hand ordinate shows the actual count obtained while the left hand ordinate shows the net count. The abcissa shows the percent of polyethylene in the simulated chest cavity. In order to obtain the actual and the net counts, counts were taken with no phantom in the background. A count of 40.5 was obtained. Thereafter, the model or empty chest cavity was inserted in front of the detector. A count of 1.164 was obtained. Thereafter, measurements were made with various percentages of the lung cavity filled with polyethylene as follows: 12.5, 25, 37.5, 50, 62.5, 75, 87.5 and 100.

FIG. 6 shows the spatial resolution of the apparatus. The results were obtained by moving a 1-inch polyethylene cube over the active surface of the test assembly. It is seen that the points are resolved to approximately one inch. As a consequence of this spatial resolution, it should be possible to build a scanner wherein the measuring probe moves below the patient to provide a scan of the chest cavity and provide a map thereof. Referring particularly to FIG. 4, such equipment could include means, such as tracks 31 and 32, for moving the source in an X and Y direction to scan the chest cavity and provide the X-Y measurements for constructing the map or two dimensional display.

The patient is not subjected to excessive radiation. Low radiation levels are possible because of the localized nature of the measurements and because sensitive detectors can be used. The radiation exposure levels with a source of $10^6$ neutrons per second at 200 KEV are given in FIG. 7. They correspond to a total exposure for a one minute measurement of approximately ½ mrem. This exposure is over a volume of approximately 27 cubic inches. The chest volume is approximately 2,000 cubic inches. The effect of a one minute measurement might be compared to a whole chest x-ray dose of about seven microrem to the entire chest. This is about fifty percent of the natural radiation received hourly.

The moderating properties and the degree of moderation of the lung can be obtained by obtaining measurements with a known moderator in place and comparing these measurements with an unknown moderator substituted therefor.

It is to be observed that the technique and apparatus can only provide a starting point for clinical application by skilled physicians. This is perhaps analagous to the application of x-ray either for medical or commercial purposes where the x-ray machine produces images which only serve as the starting point for interpretation by the specialist.

To those skilled in the art to which this invention relates, many modifications and adaptations of the invention will suggest themselves. Accordingly, the method and apparatus disclosed herein are not to be taken as limitations on the invention but as illustrative of the inventive concept. The patent is to be interpreted by the scope of the appended claims.

What is claimed is:

1. Apparatus for measuring the neutron moderation or absorption charateristics of materials, said apparatus adapted to be disposed entirely on one side of said materials comprising a source of fast neutrons, thermal neutron detecting means adapted to be disposed adjacent said materials, thermal neutron absorbing material disposed between the source of fast neutrons and said thermal neutron detecting means for passing fast neutrons to said materials, and means connected to said detecting means to provide an indication of the number of thermal neutrons received from said materials by said detecting means.

2. Apparatus as in claim 1 in which said source of fast neutrons is embedded in said thermal neutron absorbing material.

3. Apparatus as in claim 2 including a single source of fast neutrons and a plurality of detectors associated therewith.

4. Apparatus as in claim 3 in which said thermal neutron absorbing material is configured to fit within a submerged nuclear fuel storage cell.

5. Apparatus as in claim 1 in which said apparatus is adapted to be placed adjacent the chest cavity to measure the amount of water in the lung.

6. Apparatus as in claim 5 including means for moving the apparatus to scan the chest cavity.

7. Apparatus as in claim 1 including additionally a moderating means on the other side of said detector and means for removably positioning the materials whose absorption is to be measured between said detector and said moderating means to measure the thermal neutron absorption characteristics of said material.

8. The method of measuring the moderating characteristics of a neutron moderating material comprising the steps of generating fast neutrons, passing said fast neutrons through a non-moderating thermal neutron absorbing material, causing the transmitted neutrons to strike the neutron moderating material and monitoring the thermal neutron flux at the boundary between the non-moderating material and the neutron moderating material.

9. The method as in claim 8 which includes the additional step of comparing monitored neutron flux with the neutron flux from samples of the same size and known moderating characteristics.

10. The method as in claim 8 wherein the neutron moderating material comprises the lungs in the chest cavity thereby to monitor the hydrogen content of the lungs and, therefore, the water content.

11. The method for measuring the absorption characteristics of thermal neutron absorbers comprising the steps of generating fast neutrons, passing said fast neutrons through a non-moderating, inelastic scattering, thermal neutron absorber, impinging said neutrons upon a moderating material, and interposing the thermal neutron absorber between the non-moderating thermal neutron absorber and the moderating material and monitoring the thermal neutron flux near the boundary between the unknown thermal neutron absorber and no-moderating thermal neutron absorber and comparing the thermal neutron so monitored with a standard calibration curve obtained by monitoring several sheets of known thermal neutron absorbers.

* * * * *